United States Patent [19]

Muller

[11] Patent Number: 4,865,610
[45] Date of Patent: Sep. 12, 1989

[54] DEVICES FOR CONTROLLING ELECTRICALLY OPERATED APPLIANCES

[75] Inventor: Walter Muller, Binningen, Switzerland

[73] Assignee: Clayton Foundation for Research, Houston, Tex.

[21] Appl. No.: 592,041

[22] Filed: Mar. 21, 1984

[30] Foreign Application Priority Data

Dec. 4, 1983 [CH] Switzerland .................. 1956/83

[51] Int. Cl.$^4$ ............................................. A61F 2/68
[52] U.S. Cl. ................................................ 623/24
[58] Field of Search ............... 128/25 R, 316, 907; 623/24, 25, 26; 180/6.5, 167, DIG. 3; 280/242 WC

[56] References Cited

U.S. PATENT DOCUMENTS

| | | | |
|---|---|---|---|
| 2,474,200 | 6/1949 | McBee | 128/25 R |
| 2,791,999 | 5/1957 | Bustamante | 128/25 R |
| 2,885,686 | 5/1959 | Giaimo | 623/24 |
| 3,374,845 | 3/1968 | Selwyn | 180/6.5 |
| 3,769,636 | 11/1973 | Friedman | 128/28 R |
| 4,078,627 | 3/1978 | Brown et al. | 180/6.5 |
| 4,207,959 | 6/1980 | Youdin et al. | 180/6.5 |
| 4,260,035 | 4/1981 | Loveless et al. | 180/6.5 |
| 4,281,734 | 8/1981 | Johnston | 180/6.5 |
| 4,385,541 | 5/1983 | Muller et al. | 84/1.14 |

OTHER PUBLICATIONS

D. W. Lywood, "High-Speed Communication Aid For Quadriplegics", Jul. 1976, Medical & Biological Engineering, pp. 445–450.

Von H. J. Gerner, "Rollstuhiversorgung Bei Hoher Tetraplegie", Apr. 1981, Med-Orthop-Tech, pp. 97–101.

Primary Examiner—Ruth S. Smith
Assistant Examiner—John P. Lacy
Attorney, Agent, or Firm—Fulbright & Jaworski

[57] ABSTRACT

At least one actuating element emits a signal in response to blowing and/or suction airflow from a person and is connected to a mouthpiece, and is coupled by way of an evaluation circuit to the appliance to be controlled. In order to maximize the total number of possible combinations of control signal and/or control data, two position transmitters (X-pos, Y-pos) are coupled to further inputs of the evaluation circuit, which incorporates at least one microprocessor, and, when the mouthpiece is used, each transmitter emits a coordinate signal characteristic of the position of the mouthpiece in a coordinate system. The microprocessor is adapted to process the signals from the actuating element, which is in the form of an impact pressure transducer and also the coordinate signals from the position transmitters (X-pos, Y-pos) to produce control data for the appliance.

15 Claims, 4 Drawing Sheets

DEVICES FOR CONTROLLING ELECTRICALLY OPERATED APPLIANCES

BACKGROUND OF THE INVENTION

This invention relates to devices for controlling electrically operated appliances.

Such devices are particularly, but not exclusively, known as aids for people who are severely physically handicapped (see, for example "Paraplegia", official organ of the Swiss Paraplegic Foundation, 4055 Basle, year 7, No. 25, March 1983, page 16, lower illustration and accompanying caption). The known devices merely serve, for example, to actuate a light switch or to trigger an alarm call for a nurse via a switching element in the form of a relay. These known devices therefore merely carry out the function of a simple, remote-controlled "In-Out" switch, or, at best, of a change-over switch.

SUMMARY

It is an object of the invention to provide a device of the kind referred to initially, which requires actuation simply by means of the mouth of the operator, and which is capable of controlling electrically operated appliances which are appreciably more complex than a switch or the like. In this connection, the operator—as mentioned earlier—can be a person who is severely handicapped physically, e.g., a person having no arms or a paraplegic, or a person who is completely or partially unable to use his/her hands to perform manual tasks. The following are given as electrical appliances to be controlled, purely as examples and without any claim to completeness: electrically operated and guided vehicles, including wheelchairs; electrically powered artificial limbs; remote-controlled manipulators including industrial robots, typewriters, calculating systems including electronic computers and interactive electronic data processing systems.

According to the invention there is provided a device for controlling an electrically operated appliance, comprising at least one actuating element which emits a signal in response to blowing and/or suction airflow from a person and which is connected to a mouthpiece, the actuating element being coupled to the appliance to be controlled by way of an evaluation circuit, wherein two position transmitters are coupled to further inputs of the evaluation circuit, which incorporates at least one microprocessor, and, when the mouthpiece is used, each transmitter emits a coordinate signal characteristic of the position of the mouthpiece in a coordinate system, the microprocessor being adapted to process the signals from the actuating element, which is in the form of an impact pressure transducer, and also the coordinate signals from the position transmitters to produce control data for the appliance.

The coordinate system can be an orthogonal one having axes parallel to the directions of movement of the mouth of the operator, these directions corresponding to swivelling movement and nodding movement of the head. Assuming that, by swivelling the head, the mouth is capable of describing an arc of 20 cm in length, and, by nodding the head, the mouth is capable of describing an arc of 7 cm in length, and further assuming that the position transmitters exhibit a resolution of 0.5 cm of arc in each case, and that an impact pressure transducer is available which emits only one signal for suction and one signal for blowing airflow, the device is capable of emitting over 1000 discrete signal combinations. If the mouthpiece incorporates two adjacent openings (each leading to an impact pressure transducer of the kind specified) which can optionally be closed and opened by the operator's tongue, and if the position transmitters exhibit the resolution previously assumed, the number of possible signal combinations is tripled.

In one embodiment, the mounting support supporting the mouthpiece includes a rail and a sliding carriage displaceable along the rail with mouthpiece being connected to the carriage and being movable in a direction transverse to the rail. In another embodiment, the mounting support includes first and second parallelogram bar frames supporting the mouthpiece and being pivotable in plane at right angles to each other, and adapted to be attached to a person's body. Various types of position transmitters may be provided such as light sending and receiving elements, angle encoders, strain gauges, and potentiometers.

Other and further objects, features and advantages will be apparent from the following description of presently preferred embodiments of the invention, given for the purpose of disclosure and taken in conjunction with the accompanying drawings.

DESCRIPTION OF THE PREFERRED EMBODIMENTS

While the present invention will be described in connection with its application as an aid for a physically handicapped person, for purposes of illustration only, it will be understood that the present invention may be broadly used in other applications in which a person may simply by blowing and/or sucking air through a mouthpiece electrically control a variety of devices.

It should first be noted that the mouthpiece (still to be described) conforms to motions of the mouth and consequently of the head of the person operating the mouthpiece. Hereinafter swivelling movement (lateral movement to and for) of the head of the person will be designated as movement in the X direction, the instantaneous position of the head in this direction being defined as the X coordinate, whereas nodding movement (movement up and down) will be designated as movement in the Y direction, the instantaneous position of the head in this direction being defined as the Y coordinate.

Figure 1:
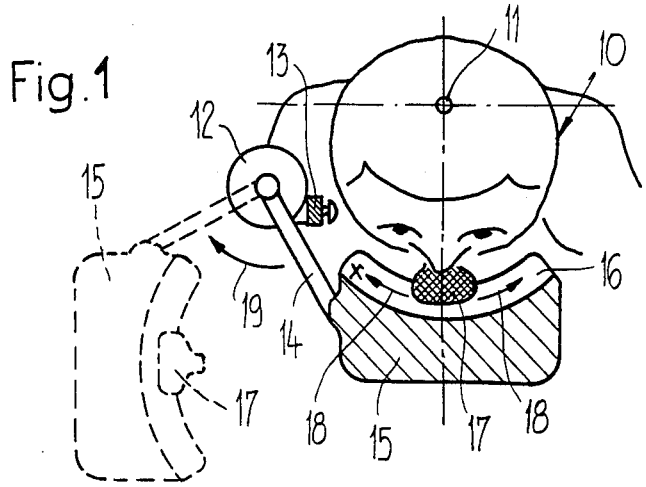
FIG. 1 is an outline view of a first embodiment of that part of the device which is to be actuated directly by the operator.

In FIG. 1 there is shown the head 10 of a person from above. The axis perpendicular to the plane of the drawing, around which the head 10 can swivel, is designated 11. A drive motor 12 is mounted on a vertical axis in a fixed position, and can be switched on and off by means of a switch 13 which can also be used to change the direction of rotation. The motor 12 carries a swivel arm 14 which can swivel in a horizontal plane and to which a mounting support 15 having an arc-shaped guide rail 16 is fixed. A sliding carriage 17 is displaceable along this guide rail 16 as shown by the arrows 18. In or on the sliding carriage 17 as will be described, there is provided a mouthpiece which the person can move with his/her mouth along the rail 16, which describes an arc around the axis 11, i.e., in the X direction. If the person actuates (for example, with his/her cheek or chin) the switch 13, after releasing the mouthpiece, the arm 14 driven by the motor 12 swivels the mounting support 15 with the sliding carriage 17 thereon clockwise (arrow 19) into the out-of-operation position shown in dotted lines in the figure and thereby disengages the person's face. A second actuation of the switch 13 brings the mounting support 15 with the sliding carriage 17 thereon back into the operating position shown in solid lines. The embodiment depicted in FIG. 1 does not have to be mounted on a fixed unit, e.g., a seat, on which the operator is positioned, but can also be fixed to the person's body. The mounting support 15 could accordingly be fitted to a frame to be fastened to the person's torso.

Figure 2:
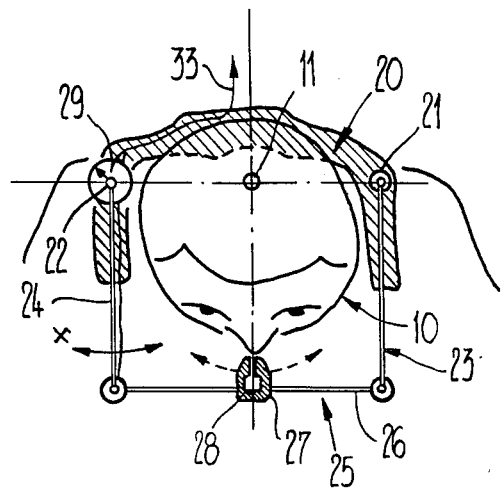
FIG. 2 is an outline view of a second embodiment of that part of the device which is to be actuated directly by the operator.
Figure 3:
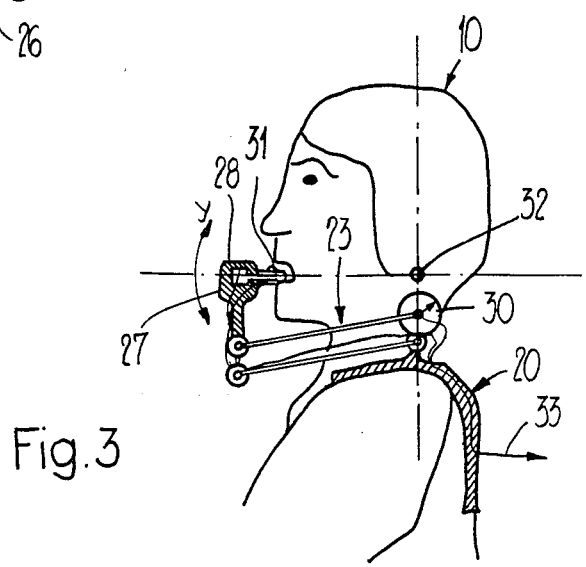
FIG. 3 is a side view of the part shown in FIG. 2.
Figure 4:
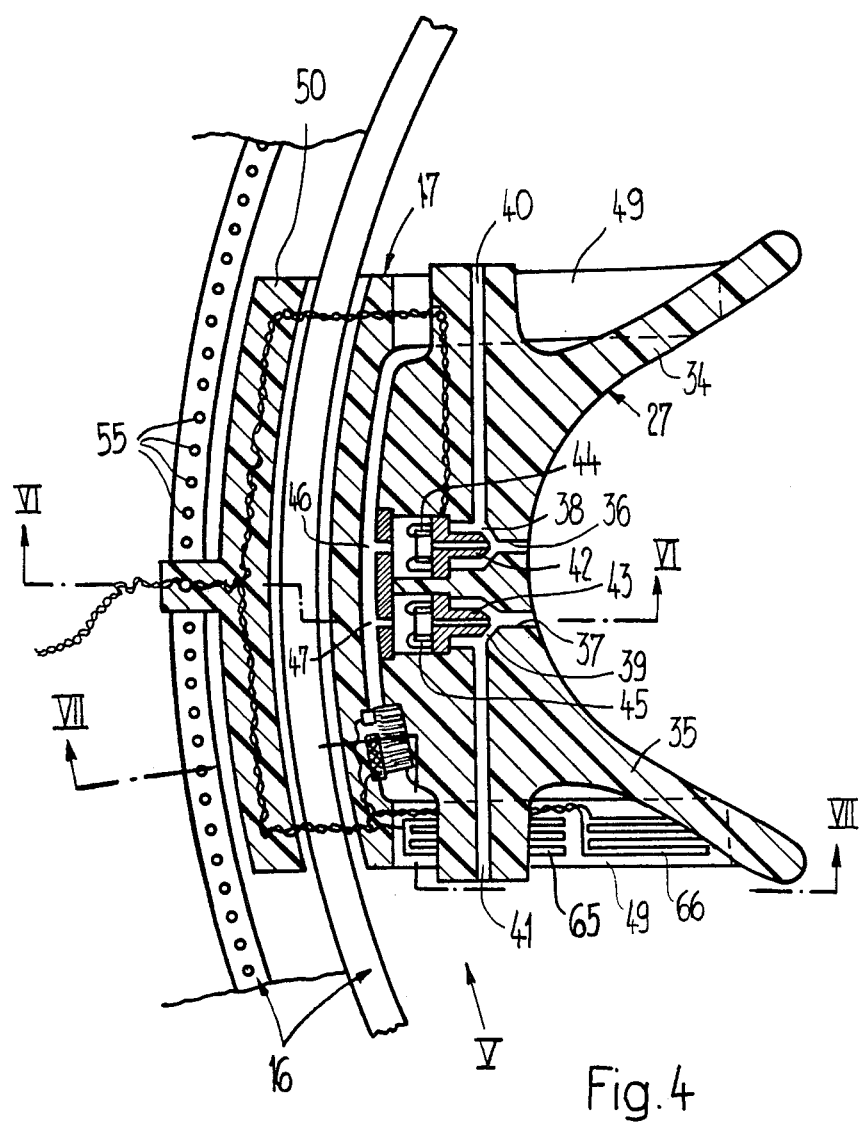
FIG. 4 is a horizontal section, on a larger scale, of the mouthpiece and related components of the part of FIG. 1, showing different variants of position transmitter.

The embodiment of FIGS. 2 and 3 is indeed fixed to the person's body and consequently moves with the latter's torso. For this application, a frame 20 emcompassing the person's neck and shoulders, and anatomically fitted to the wearer, is provided. The frame 20 is appropriately lashed to the person's trunk with straps (not shown). The parts of the frame 20 which fit over the shoulders have end members 23 and 24 of a first parallelogram bar frame 25 fixed thereto, the end members each being pivotable about a respective ball joint 21 and 22, and the central member 26 of the parallelogram having a mouthpiece 27 fastened to it. An impact pressure transducer 28, shown here in outline only in the first instance, is incorporated in the mouthpiece 27. The vertical axis of rotation 22 of the end member 24 is at the same time the axis of an angle transmitter 29, e.g., of a potentiometer or of an angle encoder, which thus emits an electrical signal corresponding to the angle of swivelling of the parallelogram bar frame 25 in the horizontal plane. One of the end members of the parallelogram bar frame 25, e.g., the end member 23, is for its part configured, as can be inferred from FIG. 3, as a parallelogram bar frame that can be swivelled in a vertical plane, whose upper bar actuates a further angle transmitter 30, which for its part emits a signal corresponding to the angle of swivelling of the bar frame 23 in the vertical plane. The lengths of the bars of the frames 23 and 25 are chosen such that movement of the mouthpiece 27, which can be fitted with a bite contact 31, by the person's mouth describes arcs which are centered on the axis 11 and the axis 32 (the axis of the nodding motion of the head 10).

In addition to the signals emitted by the impact pressure transducer 28, and if need be by the bite contact 31, the angle transmitters 29 and 30 additionally each emit a signal characterizing the X or the Y direction, and all these signals are transmitted by a conductor cable 33 shown in outline only.

The mouthpiece will now be described in more detail, particularly as to its mode of installation in the sliding carriage 17 of FIG. 1, with reference to FIGS. 4 to 7. The mouthpiece 27 of FIGS. 2 to 3 in the narrower sense can be configured similarly to the mouthpiece depicted in FIGS. 4 to 7.

The mouthpiece illustrated comprises two lateral lobes 34 and 35 shaped in the manner of a mouth mask, which are intended to rest fully on the parts of the cheeks adjacent to the corners of the person's mouth. In the central area between the lobes 34, 35, two blowing-/suction openings 36 and 37 are provided, each debouching into a chamber 38 or 39 respectively. From each of the chambers 38 and 39, an air vent 40 or 41 with a throttled, preferably adjustable throughput capacity leads out into the open. Also a connecting fitting 42 or 43 is provided in each chamber 38 or 39. The connecting fittings 42 and 43 connect the chambers 38 and 39 in each case with the one side of an impact pressure transducer 44 or 45 (for example, product No. 140 PC, Type D, Micro Switch Corporation) whose other side is connected with the outside via a pressure equalization vent 46 or 47. Each of the impact pressure transducers 44 and 45 generates a signal characterizing by value and arithmetical sign the pressure differential between the chambers 38, 39 and the outside.

Figure 5:
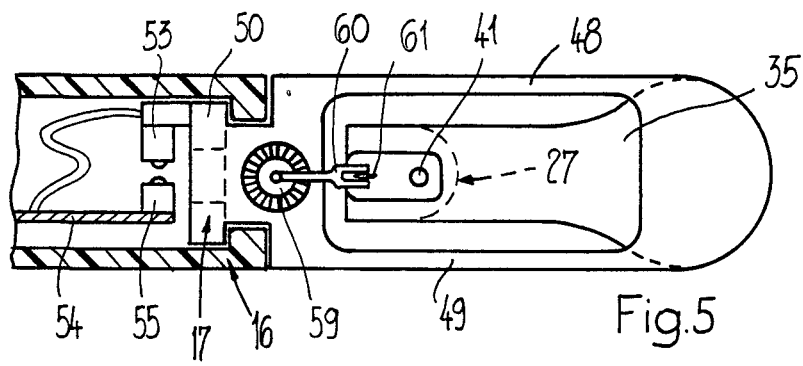
FIG. 5 is a view, partly in section, in the direction of the arrow V in FIG. 4.
Figure 7:
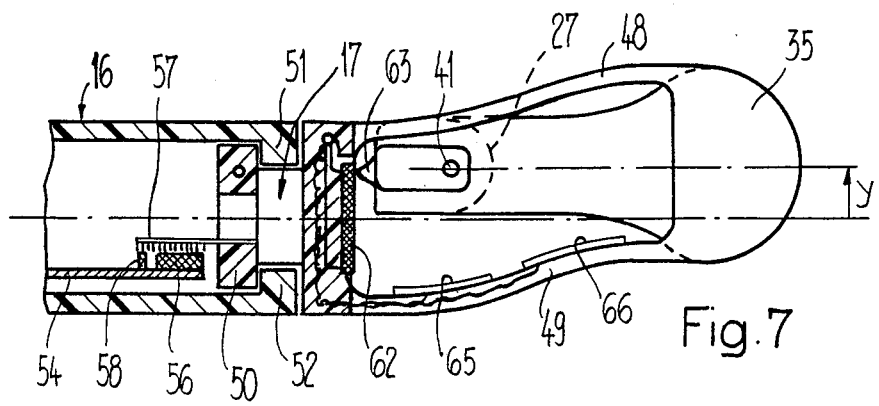
FIG. 7 is a section taken along the line VII—VII in FIG. 4, with the mouthpiece moved upwards from the rest position and showing other variants of the two position transmitters.

As can be inferred in particular from FIGS. 5 and 7, the mouthpiece 27 is connected to the sliding carriage 17, which itself is displaceable along the arc-shaped guide rail 16, via two pairs of leaf springs 48 and 49 fitted one above another and made from synthetic material for example. The upper and lower leaf springs 48 and 49 are fixed at one end to the sliding carriage 17 and at the other end to the free end regions of the side lobes 34 and 35, and thereby make it possible for the mouthpiece 27 to be displaced or deflected transversely to the track of the guide rail 16 and against the effect of the leaf springs, i.e., in the Y direction. The manner in which this movement is detected will be described below.

Figure 6:
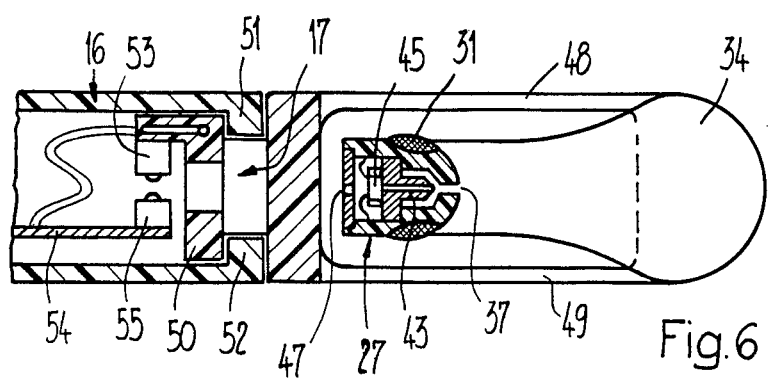
FIG. 6 is a section taken along the line VI—VI in FIG. 4.

The sliding carriage 17 comprises an arc-shaped extension 50 which is T-shaped in cross-section and is secured behind two flanges 51 and 52 which face each other, and are formed on the guide rail 16, as shown in FIGS. 6 and 7. A light source 53, which in practice takes the form of a point source, e.g., a light emitting diode (LED), is fixed to the extension 50. Immediately opposite the light source 53 are light-sensitive elements 55, e.g., phototransistors, arranged on a support 54 which is fastened to the mounting support and consequently is in a fixed position relative to the guide rail 16, the elements 55 being in a row concentric with the arc of the guide rail 16. The light source 53 accordingly forms, with the row of light-sensitive elements 55, the position transmitter for the X direction, insofar as the light source 53 is able to actuate at any given time only one of the elements 55, which for its part indicates the instantaneous position of the sliding carriage 17 in the X direction.

As shown in FIG. 7, the position transmitter for the X direction can alternatively be formed by a resistive layer 56 running parallel to the arc of the rail 16 and swept by a sliding contact 57 fixed to the extension 50. The sliding contact 57 also sweeps a slip ring segment 58, parallel to the resistive layer 56 but insulated from it, so that the resistance value between the one end of the resistive layer 56 and the slip ring segment 58 depends on the instantaneous position in the X direction of the sliding carriage 17 and hence of the mouthpiece 27. The layer 56, the sliding contact 57 and the slip ring segment 58 thus together form a position transmitter for the X direction, which in this case emits an analogue signal characterizing the X position.

It has already been stated that the mouthpiece 27 can be moved or deflected upwards and downwards relative to the sliding carriage and against the effect of the leaf springs 48 and 49, that is, transversely to the track of the rail 16. The direction of this movement is the Y direction (in FIG. 7 the mouthpiece 27 is at maximum deflection upwards). In order to detect this movement or deflection in the Y direction, an angle encoder 59 is fixed to the sliding carriage 17 in FIG. 5. This angle encoder 59 can be actuated via a forked arm 60 which itself embraces a pin 61 fixed to the side of the mouthpiece 27. The angle encoder 59 thereby forms the position transmitter for the Y direction.

As shown in FIG. 7, the position transmitter for the Y direction can alternatively be formed by a potentiometer which consists of a resistive layer 62 fixed to the sliding carriage 17 and swept by a sliding contact 63 fitted to the mouthpiece 27. The resistance value between one end of the resistive layer 62 and the sliding contact 63, or alternatively the resultant voltage drop across the elements, generates an analogue signal characterizing the instantaneous position of the mouthpiece 27 in the Y direction.

Another form of position transmitter for the Y direction is also shown in FIG. 7 (and also in FIG. 1). When the mouthpiece 27 is moved or deflected transversely to the guide rail 16, the leaf springs 48 and 49 bend in an "S" shape, as shown in FIG. 7. This bending causes one part of the surface of each leaf spring to stretch and another part of the same surface to be compressed, the extent of stretching and/or compression being a measure of the deflection of the mouthpiece 27 in the Y direction. Two strain gauges 65 and 66 fixed to one of the lower leaf springs 49 may therefore serve as the position transmitter for the Y direction, and may generate an analogue output signal.

The elements located in the vicinity of the operator's mouth which have been described provide the following signals:

impact pressure transducer 28 and/or 44, 45: pressure differential in one, or in two separated, chambers with respect to the outside (produced by blowing or suction through the openings 36 and/or 37).

angle transmitter 29 (FIG. 2) or LED 53 and phototransistors 55 (FIG. 4) or potentiometers 56, 57, 58 (FIG. 7): instantaneous position of the mouthpiece in the X direction.

angle transmitter 30 (FIG. 3) or angle encoder 59 (FIG. 5) or potentiometers 62, 63 (FIG. 7) or strain gauges 65, 66 (FIGS. 1, 7): instantaneous position of the mouthpiece in the Y direction.

bite contact 31 (FIGS. 3 and 6): additional switching signal.

It goes without saying that these diverse signals have to be processed into data which is suitable for bringing into operation the appliance which is to be controlled. Likewise it will be appreciated that the evaluation circuit required for this purpose has to be adapted not only to the type of impact pressure transducer or pressure measuring cell and of position transmitter, but also to the type of appliance to be controlled, and finally also to the perhaps impaired abilities of the operator who is to operate the device.

Figure 8:
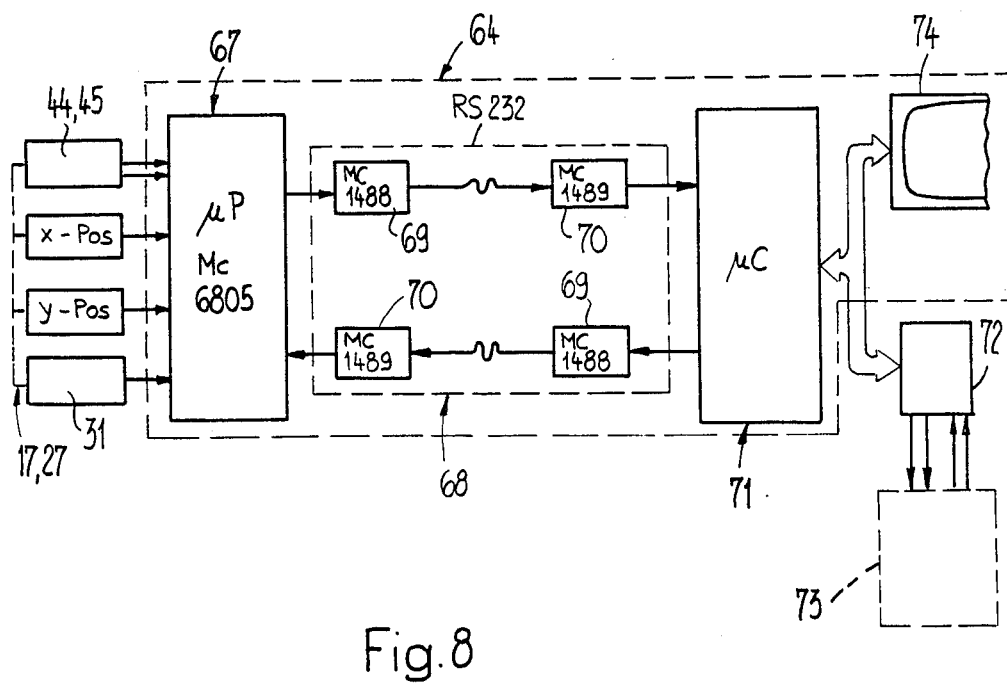
FIG. 8 is a simplified block diagram of an evaluation circuit.

A possible evaluation circuit for this purpose is shown in FIG. 8, and designated 64, the circuit being shown in highly diagrammatic form and purely by way of example.

The input stage, as it were, of the evaluation circuit 64 is constituted by a microprocessor 67 (e.g., Motorola product type MC6805, or Intel product type 8048) in which, in addition to a central processing unit (CPU), a working memory (RAM), a fixed-programmed memory (ROM) and analogue-digital as well as digital-analogue converters with the associated inputs and outputs are integrated. On the input side, the following are connected to the microprocessor: the impact pressure transducers 44, 45 (or 28), the position transmitters for the X and Y directions (here designated X-pos and Y-pos), and the bite contact 31 (if present).

The programme in the fixed-programme memory performs the following functions in the example represented:

reception of the digital and analogue signals whenever they are received from the transmitters.

digitisation of the analogue signals.

evaluation and processing of the digitised signals into data according to the requirements of the appliance to be controlled, and output of the data in serially coded form.

An interactive standard interface 68 of the RS232 type (enclosed by dotted lines in FIG. 8) can be connected to the microprocessor 67, or, for each direction of data flow, a respective drive module 69 (e.g., Motorola MC1488) may be coupled to a respective receive module 70 (e.g., Motorola MC1489), the coupling between the drive and receive modules being either by way of a conductor or even by a wire-less connection.

A microcomputer 71 is connected to the interface 68 or to the modules 69, 70, being on the one hand adapted to steer (via a further interface 72) the appliance to be controlled, and on the other hand connected to a peripheral unit, e.g., in the form of a VDU 74. This VDU 74 is positioned in the field of view (directly or via a projection system) of the operator of the device. On the VDU 74 there may appear, for example, the operations executed by the appliance 73, in textual or symbol form, plus a cursor which specifies the instantaneous position of the mouthpiece 27 in the X, Y coordinate system. If the cursor is superimposed on an operational text of symbol, corresponding operation of the appliance 73 can be induced, for example by blowing and/or suction, in which case termination of operation is then also indicated on the VDU 74.

If, for example, the appliance is a typewriter or an electronic data processing installation, the corresponding keyed input would appear on the VDU together with, if necessary for the purpose of any corrections that may be required, a specified quantity of the data previously inputted.

As already mentioned, the evaluation circuit 64 has to be adapted to the kind of transmitters used on the input side, and to the nature of the appliance to be controlled, in which case the fixed programme of the microprocessor 67 and, if necessary, the programme of the microcomputer 71 can also be adapted to the capabilities of the operator. The structure of the evaluation circuit 64 can accordingly be very varied, depending on the appliance to be controlled. It is important in the configuration described that, with the impact pressure transducer(s), and the position transmitters coupled directly or indirectly to the mouthpiece, a virtually unlimited number of signals can be generated, which can be processed into the data necessary and suitable for the control of complex appliances.

The device described can accordingly be regarded as a valuable aid to the full reintegration and rehabilitation of people who are physically severely handicapped, and/or as a contribution to the facilitation or simplification of the execution of complex control processes.

The present invention is therefore well adapted to carry out the objects and attain the ends and advantages mentioned as well as others inherent therein. While a preferred embodiment of the invention has been given for the purpose of disclosure, numerous changes in the details of construction and arrangement of parts will readily suggest themselves to those skilled in the art and which are encompassed within the spirit of the invention and the scope of the appended claims.

What is claimed is:

1. A device for controlling an electrically operated appliance comprising,
   a movable moputhpiece adapted to conduct an air flow therethrough in response to a person blowing and/or sucking air therethrough,
   a pressure transducer connected to the mouthpiece and actuated by air flow through the mouthpiece, said transducer providing a signal in response to air flow,
   two position transmitters connected to and measuring the position of the mouthpiece in a coordinate system, each transmitter emitting a coordinate signal characteristic of the position of the mouthpiece in a coordinate system,
   an evaluation circuit connected to and receiving the outputs of the pressure transducer and the position transmitters, said circuit including at least one microprocessor for processing the output signals from the pressure transducer and the position transmitters, said circuit connected to and controlling said appliance.

2. The device of claim 1, including a mounting support connected to the mouthpiece which is capable of being brought into a fixed position relative to the body of an operator, and the mouthpiece is movable relative to the mounting support in two coordinate directions, each of which is detectable by the position transmitters.

3. The device of claim 2, wherein the mounting support includes a rail and a sliding carriage displaceable along the rail, the mouthpiece being connected to the carriage and being movable in a direction transverse to the rail.

4. The device of claim 3, including a row of position sensors disposed along the rail, the sensors cooperating with an element fitted to the sliding carriage and the sensors and the element together constituting one of the position transmitters.

5. The device of claim 3, wherein the rail is horizontally positioned and arc shaped.

6. The device of claims 3 or 4, wherein the mouthpiece is connected to the sliding carriage by way of at least one spring element which is capable of being deformed transverse to the rail, and said other position transmitter incorporates at least one strain gauge connected to the spring element.

7. The device of claim 4, wherein the position sensors fitted to the rail are light-sensitive elements arranged to be actuated by a light source fitted to the sliding carriage.

8. The device of claim 3, including a resistance mounted on the rail and a sliding contact on the sliding carriage coacting to form a potentiometer constituting one of the position transmitters.

9. The device of claim 2, wherein the mounting support comprises a first parallelogram bar frame, which is capable of being swivelled in a first plane and whose end members are capable of being attached to the person's body, a second parallelogram bar frame being formed by at least one of the end members of the first parallelogram bar frame and pivotable in a plane at right angles to the first plane, and the mouthpiece fixed to an intermediate member of the first parallelogram bar frame, the position transmitters being angle transmitters connected to and adapted to detect the angle of swing of both parallelogram bar frames.

10. The device of claim 1, wherein the pressure transducer provides a value signal to the microprocessor.

11. The device of claims 1, or 2, or 3, or 4, or 5 wherein the mouthpiece is provided with a bite contact which is also coupled to the evaluation circuit.

12. The device of claim 3, including a swivel arm supporting the rail for movement between an operating position and a rest position.

13. The device of claim 12, including a motor connected to the swivel arm for moving the swivel arm from the operating position into the rest position, and a switch actuable by the operator's head and connected to and actuating the motor.

14. The device of claims 1, or 2, or 3, or 4, or 5 including a display unit coupled to the evaluation circuit and having a cursor which, in conjunction with the operation of the appliance to be controlled, indicates the instantaneous position of the mouthpiece in the coordinate system.

15. The device of claims 1, or 2, or 3, or 4, or 5 wherein the mouthpiece incorporates two blowing openings which are immediately adjacent one another and are connected to the pressure transducer whose output is supplied to an input of the evaluation circuit.

* * * * *

UNITED STATES PATENT OFFICE
CERTIFICATE OF CORRECTION

Patent No. 4,865,610        Dated September 12, 1989

Inventor(s) Walter Muller

It is certified that error appears in the above-identified patent and that said Letters Patent is hereby corrected as shown below:

Column 2, line 62, delete "for" and insert -- fro --

Column 7, line 21, delete "moputhpiece" and insert -- mouthpiece --

Signed and Sealed this

Eleventh Day of September, 1990

Attest:

HARRY F. MANBECK, JR.

Attesting Officer           Commissioner of Patents and Trademarks